United States Patent
Viscomi et al.

(10) Patent No.: US 8,584,298 B2
(45) Date of Patent: Nov. 19, 2013

(54) DISPOSABLE FINGER MOUNTED INSTRUMENT CLEANER

(76) Inventors: Brian D. Viscomi, Easton, PA (US); Dominic Anthony Viscomi, Easton, PA (US); Julie Glazer, Paramus, NJ (US)

( * ) Notice: Subject to any disclaimer, the term of this patent is extended or adjusted under 35 U.S.C. 154(b) by 1201 days.

(21) Appl. No.: 12/228,344

(22) Filed: Aug. 12, 2008

(65) Prior Publication Data

US 2008/0311543 A1    Dec. 18, 2008

Related U.S. Application Data

(63) Continuation-in-part of application No. 11/726,332, filed on Mar. 21, 2007, now Pat. No. 8,136,194.

(60) Provisional application No. 60/813,025, filed on Jun. 13, 2006.

(51) Int. Cl.
*A61C 3/00* (2006.01)
*B01B 1/00* (2006.01)

(52) U.S. Cl.
USPC ....... 15/104.92; 15/209.1; 15/210.1; 63/15.5; 63/15.6; 63/15.65; 206/63.5; 224/218; 433/49; 433/163

(58) Field of Classification Search
USPC ........ 15/104.92, 209.1, 210.1, 167.3; 433/49, 433/163; 206/62.5; 224/218; 63/15.5, 15.6, 63/15.65

IPC ....................................... A61C 3/00; B08B 1/00
See application file for complete search history.

(56) References Cited

U.S. PATENT DOCUMENTS

| | | | | |
|---|---|---|---|---|
| 3,204,426 | A | * | 9/1965 | Armstrong ...................... 63/15.5 |
| 4,844,308 | A | * | 7/1989 | Porteous ........................ 224/217 |
| 5,169,315 | A | * | 12/1992 | Bull .............................. 433/163 |
| 5,368,482 | A | * | 11/1994 | Johnsen et al. ................ 433/163 |
| 6,036,490 | A | | 3/2000 | Johnsen et al. |
| 6,257,888 | B1 | * | 7/2001 | Barham ........................ 433/163 |
| 6,971,879 | B2 | * | 12/2005 | Discko, Jr. .................... 433/163 |
| 6,986,924 | B2 | | 1/2006 | Croll |
| 7,014,463 | B2 | | 3/2006 | Savoia |

* cited by examiner

*Primary Examiner* — David Redding

(57) ABSTRACT

A finger mounted instrument cleaner (2) of the type having an elongated semi-circumferential protective body (4) to desirably wrap around a finger. The protective body (4) has a volume of absorbent foam or cleaning member (22) thereon and a securing means to engage a finger. The securing means comprises a semi-circumferential finger clasp (12) pivotably conjoined to a first side of said protective body by a flexible juncture or flexion pivot (10) and a clasp securing extension (18) contiguous to an opposing second side of said protective body. The finger clasp (12) and clasp securing extension (18) have a predetermined number of ratchet teeth formed thereon. Desirably pivoting said engaging clasp (12) to communicate with clasp securing extension (18) engages the ratchet teeth to form a variably interlocking circumferential union with said protective body (4).

2 Claims, 19 Drawing Sheets

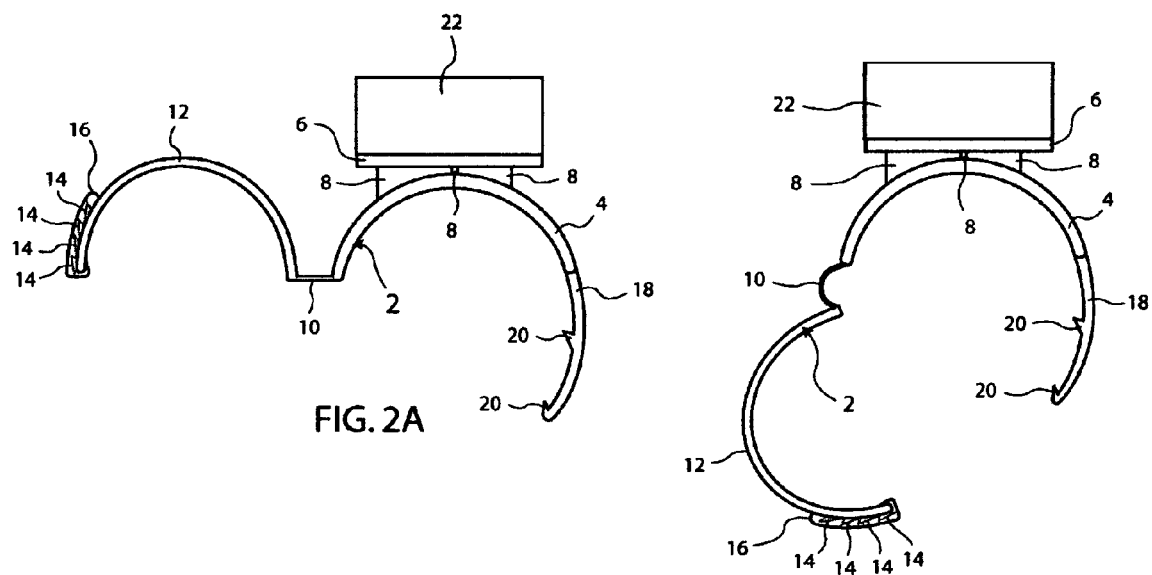
FIG. 2A
FIG. 2B
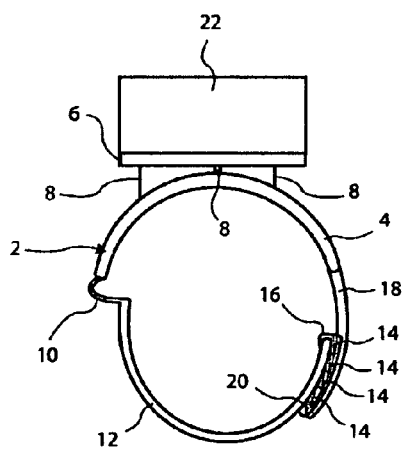
FIG. 2C

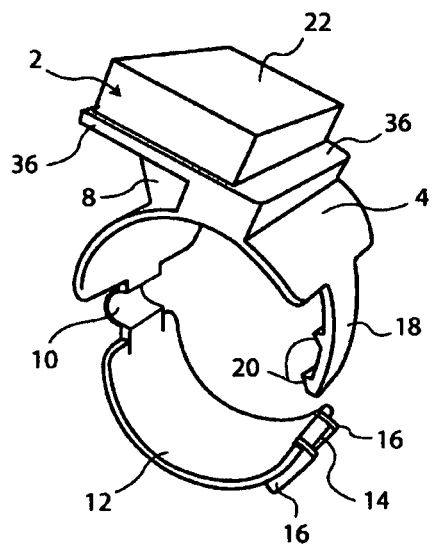
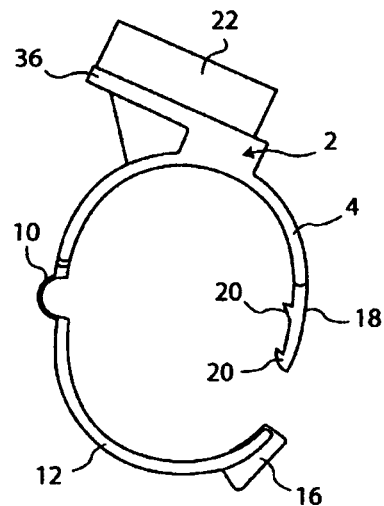
FIG. 9A  FIG. 9B
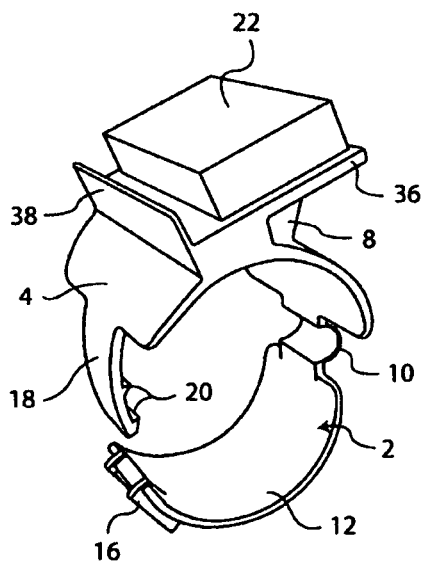
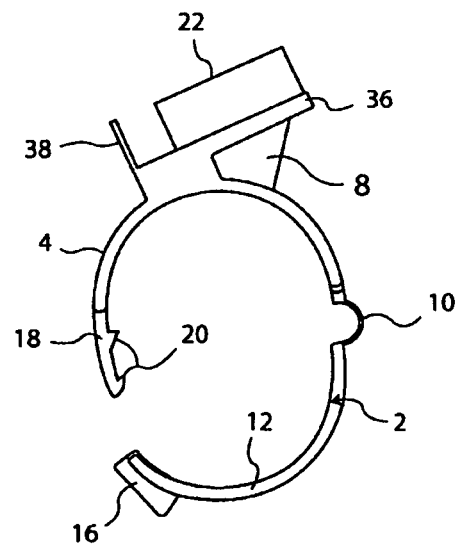
FIG. 10A  FIG. 10B

DISPOSABLE FINGER MOUNTED INSTRUMENT CLEANER

CROSS REFERENCE TO RELATED APPLICATIONS

This application is a continuation in part and claims the benefits of Provisional Patent Application Ser. No. 60/813,025, filed 2006 Jun. 13, and non-provisional application Ser. No. 11/726,332 filed 2007 Mar. 21, now U.S. Pat. No. 8,136,194 by the present inventors

FEDERALLY SPONSORED RESEARCH

Not Applicable

SEQUENCE LISTING OR PROGRAM

Not Applicable

BACKGROUND

1. Field of Invention

This invention applies to the fields of Dentistry and Medicine in particular to allow for the ergonomic cleaning of and application of medications and or disinfectants to operative hand instruments in a protective manner concurrent with performing a procedure.

2. Prior Art

Dentistry and its medical counterpart may avail of this invention's novelty regarding chair-side procedures, and specifically those procedures which require the close proximity of both hands. In Dentistry, typically during the scaling phase of a dental prophylaxis, the Hygienist will retain a cleaning cloth (gauze sponge) within the fingers of the hand opposite that of the one employing the instrument. When not cleaning the instrument head, these fingers often times are in use to hold an auxiliary instrument or to retract oral structures (cheek, tongue, lips). To clean the debris laden (blood and calculus) instrument, the operator must make a deliberate hand (rotation) and fingers (compression of the instrument working end within the confines of the gauze sponge) adjustment. This maneuver among other things causes a disruption during the procedure with constant hand repositioning and interrupts the usage of that hand. Also the instrument potentially can be wiped by an area in the gauze previously laden with contaminated bacterial debris with the likelihood of reintroducing pathogens back into the periodontal structures (gums). There is also opportunity to experience an inadvertent self-induced instrument stick with its subsequent unwanted sequelae. The fingers-holding gauze technique also precludes the instrument holding ability of that hand. Although this scenario represents the standard protocol in a typical dental prophylaxis procedure, there does exist alternative ways to by-pass the fingers and gauze technique.

U.S. Pat. No. 4,844,308 to Porteous, Don D., Jul. 4, 1989 presents a finger mounted cup designed to hold dental paste or tooth cleaning agent. It permits an instrument to access and procure its contents but does not provide for instrument cleaning and debridement.

U.S. Pat. No. 5,368,482 to Johnsen, James B., Nov. 29, 1994 presents a finger mounted dental instrument servicing system for instrument cleaning and to transfer a medicament to an operative site. It is composed of disposable and non disposable components. Its myriad of components i.e. wiping sponge, appendage to hold cleaning medicaments and root canal file measuring scale can present the operator with ergonomic challenges. Furthermore, the components rest upon a horizontal platform which dictates an optimal position on the operator's finger in order to be most accessible. The instrument cleaning sponge presents a homogenous surface which can impede instrument insertion and withdrawal. The non disposable component also presents with cleaning and sterilization considerations.

U.S. Pat. No. 6,257,888 to Barham, William L., Jul. 10, 2001 presents as an instrument cleaning device and a separate polish dispensing receptacle. This device is adhesively secured to back of the hand which necessitates deliberate hand rotation to access and does not permit aggressive engagement of the instrument head to remove stubborn debris.

U.S. Pat. No. 6,036,490 to Johnsen, James B., Mar. 14, 2000 also presents as a dental instrument servicing device. However, the application for this device is intended for Endodontic (root canal) therapy. Its plurality of components precludes its practicality for non-endodontic procedures.

U.S. Pat. No. 6,971,879 to Discko, John J. Jr., Dec. 6, 2005 claims a material dispensing instrument cleaning sponge. This sponge presents with a singular slit and an adhesive backing as a preferred means of attaching to the hand. Hence, relocation or adjusting may compromise the sponge's integrity and or cause unwanted expression of the sponge's fluid contents. Also, to avail of multiple cleaning grooves it is necessary to affix additional sponges to the hand. Furthermore this device promotes itself for delivery exclusively for low viscosity agents, precluding its ability to contend with those of a highly viscous nature.

U.S. Pat. No. 6,986,924 to Croll, Theodore P., Jan. 17, 2006 presents a semi-rigid adhesively attached finger mounted receptacle to facilitate the delivery of pastes and solution and does not function in the capacity of instrument debridement or finger protection.

U.S. Pat. No. 7,014,463 to Savola, Dominic, Mar. 21, 2006 presents as a device which relies on a circular tuft of bristles to engage and debride instrument heads. It doe not purport to retain or dispense pastes or medicaments. Furthermore it does not allow for instrument decontamination.

Accordingly, several advantages of the present patent application of Brian D. Viscomi, Dominic A. Viscomi, and Julie A. Glazer for finger mounted instrument cleaner are:

(a) Anatomically contoured to conform to individual's finger shape and size
(b) Provides circumferential work field close to operative field
(c) Circumferential design provides for greater surface area
(d) Guards against accidental finger stick
(h) Cleans and disinfects working end of instrument
(i) Provides as a vehicle for introducing medicated solutions into the operative area
(j) Can provide for the introduction of topical anesthetic to the operative site
(k) Ergonomic placement and design promotes efficiency and lessens hand fatigue
(l) Esthetic streamlined appearance
(m) One size fits all and is disposable

SUMMARY OF THE INVENTION

It is thus the object of this invention to provide a disposable, generally circumferential finger mounted dental or medical chair-side instrument cleaning device. It is the further aim of this invention to disinfect the instrument's operative end during the process. Another object of this invention is to provide additional protection to the operator against inadvertent instrument sticks. Accordingly, a finger mounted device which can be impregnated with an appropriate solution to clean and disinfect an operative instrument in a protected manner while allowing the clinician to function with minimal disruption of hand movements during the operative procedure.

DRAWINGS

Figures

FIGS. 2A to 2C show progressive orthographical views of the finger securing clasp engaging the finger guard's clasp securing extension.

FIGS. 9A to 9B show an alternative embodiment having a desirably angled swiping platform.

FIGS. 10A to 10B show an alternative embodiment having an angled swiping platform with a protective instrument deflection guard.

REFERENCE NUMBERS

| | |
|---|---|
| 2. | Finger mounted instrument cleaner |
| 4. | Finger guard |
| 6. | Swiping platform |
| 8. | Platform support |
| 10. | Flexion Pivot |
| 12. | Finger clasp |
| 14. | Finger clasp ratchet |
| 16. | Ratchet stabilizer |
| 18. | Clasp securing extension |
| 20. | Clasp securing ratchet |
| 22. | Cleaning foam |
| 24. | Adhesive layer |
| 26. | Operator |
| 28. | Medicament |
| 30. | Operative instrument |
| 32. | Dentition |
| 34. | Accumulated debris |
| 36. | Angled swiping plane |
| 38. | Instrument deflection guard |
| 40. | Concave swiping plane |
| 42. | Variably angled swiping plane |
| 44. | Finger gripping contours |
| 46. | Gripping coil |
| 48. | Flexion gap |
| 50. | Adhesive securing strap |
| 52. | Peel away cover |
| 54. | Securing adhesive |
| 56. | Adhesive securing expanse |
| 58. | Snapping extrusion |
| 60. | Snapping aperture |
| 62. | Pivot hinge |
| 64. | Debris trap |

DETAILED DESCRIPTION

FIGS. 1A TO 4C

Figure 1A:
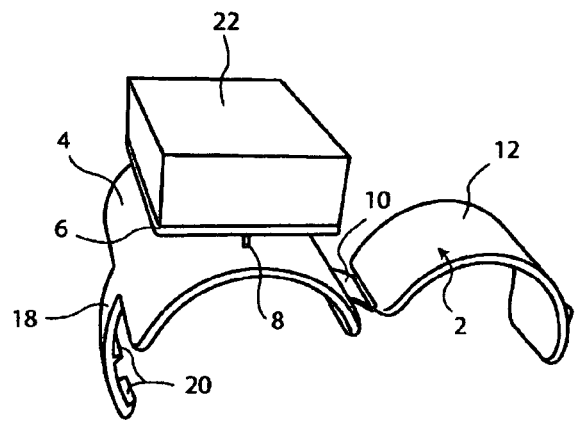
FIGS. 1A to 1C show various views of the preferred embodiment having a semi-cylindrical finger guard, a swiping platform with an adhered cleaning foam volume, clasp securing extension, and pivoting finger clasp with ratchet teeth.
Figure 1B:
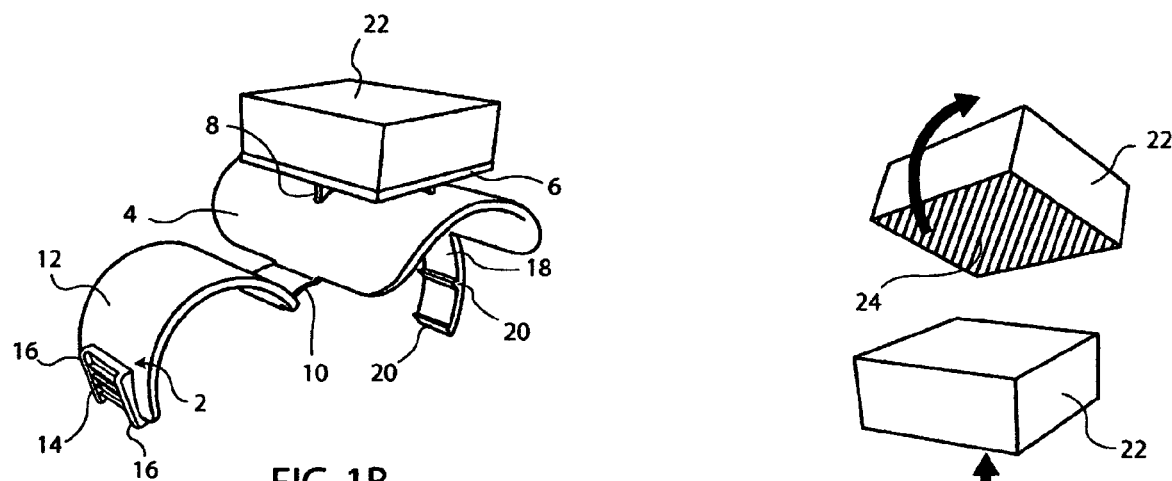
Figure 1C:
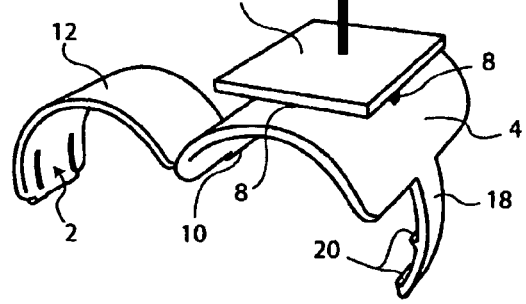
Figure 3A:
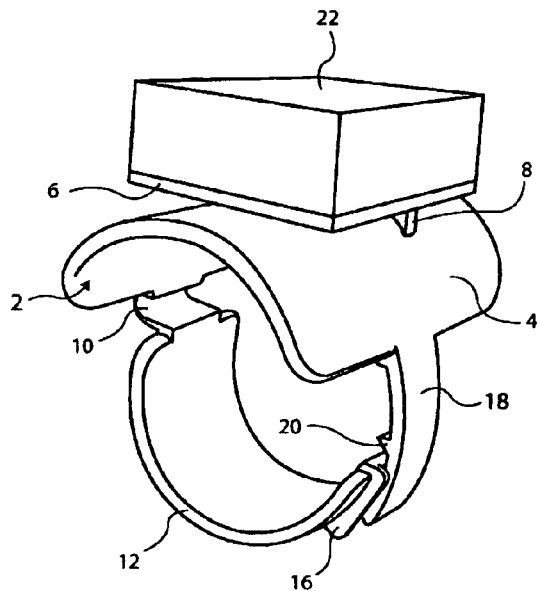
FIGS. 3A and 3B show anterior and posterior dimensional views of an instrument cleaner with the finger clasp engaged with the clasp securing extension to form an interlocking circumferential union with the finger guard.
Figure 3B:
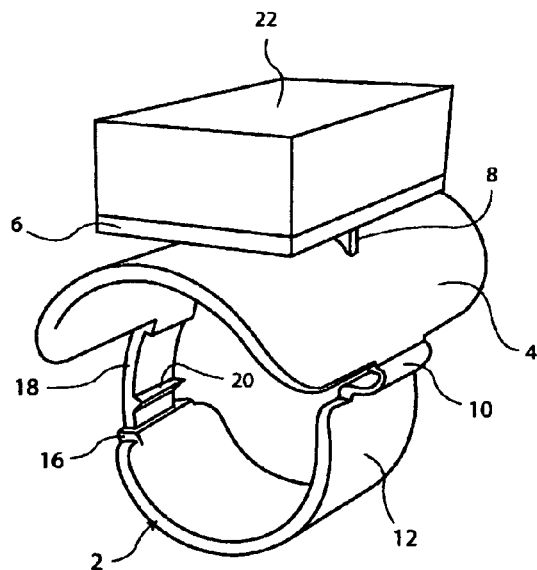
Figure 4A:
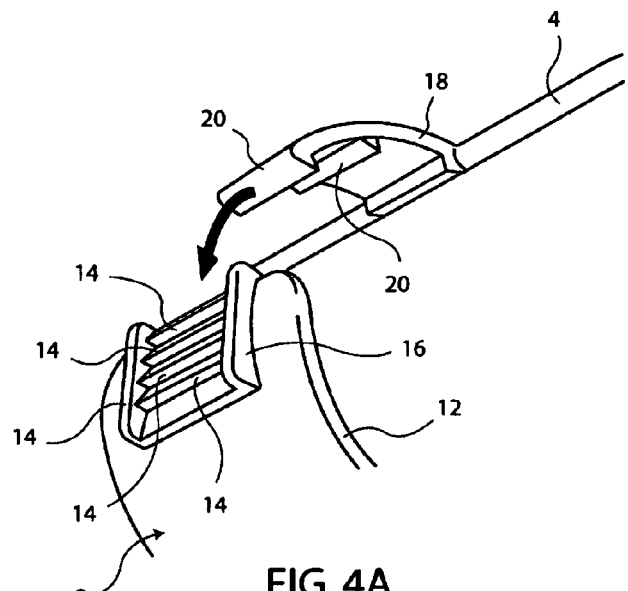
FIGS. 4A to 4C show various close-up views of the finger clasp ratchet forming an interlocking union with the securing extension's clasp securing ratchet.
Figure 4B:
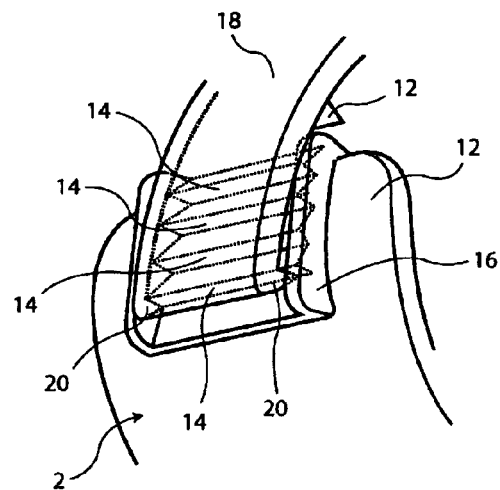
Figure 4C:
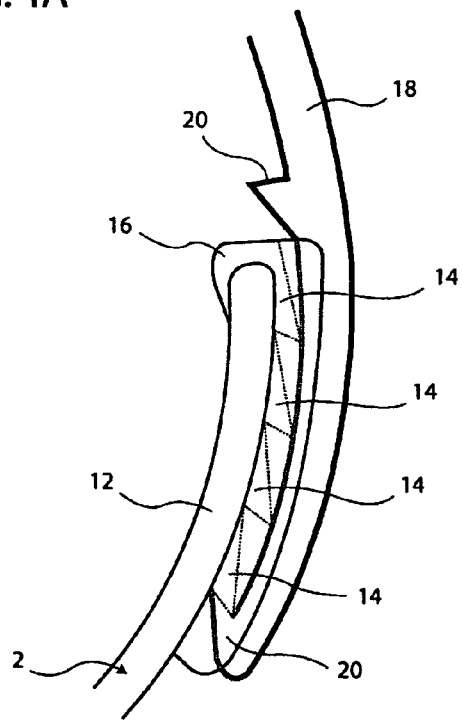

FIGS. 1A to 1C show various views of a finger mounted instrument cleaner 2 in an open, non-circumferentially interlocked position. FIGS. 2A to 2C show a progressive orthographical sequence of a finger mounted instrument cleaner 2 forming a circumferential interlocking union. FIGS. 3A to 3B show anterior and posterior dimensional views of a finger mounted instrument cleaner 2 circumferentially interlocked. FIGS. 4A to 4C show detailed close-up views of an instrument cleaners 2 locking system.

The finger mounted instrument cleaner 2 is a protective ring designed to adjustably interlock around a finger. It is comprised of two primary portions. The first portion is a desirably puncture resistant injection molded plastic body with articulating features. This injection molded plastic body consists of a semi-cylindrical, convex expanse or finger guard 4, a secondary semi-cylindrical expanse or finger clasp 12 and a clasp securing extension 18 to engage the finger clasp 12. Both the finger clasp and clasp securing extension feature an interlocking ratchet system that facilitates a variably circumferential interlocking union when they are articulated and engaged. The instrument cleaner's 2 second portion is a desirably absorbent volume of open cell foam or cleaning foam 22. The cleaning foam 22 is appropriately sized designed to adhesively correlate with the finger guard 4 (FIG. 1C).

Elaborating further, the finger guard 4 is a convex semi-tubular form that is intended to semi-circumferentially correlate with the extensor and lateral portions of a finger. The length and degree of wraparound is desirably sufficient to occlude the most vulnerable aspects while maintaining optimal finger flexion. When worn on a finger, the finger guards 4 coverage encompasses the entire extensor region and wraps around to about half way down the lateral portions of a finger. Furthermore, the finger guard's 4 length desirably extends from the knuckle portion of a finger to a distance beyond the finger's first phalange.

Positioned on the superior region of the finger guard 4 is a continuously attached and elevated planar surface or swiping platform 6. The platform 6 is a flat expanse with a rectangular dimension that is connected to the finger guard via a series of supporting struts or platform supports 8. The swiping platform's planar surface 6 serves as an adhesive anchoring point for the cleaning foam 22 (FIG. 1C). Furthermore, the flat surface bolsters the cleaning foam 22 adhesion by discouraging possible cleaning foam 22 de-lamination, that may occur more readily on a curved surface (potential de-lamination instigated by inherent foam memory exacerbated with use of medicated wetting agents). Lastly, the platform 6 is desirably thick to ensure operational rigidity and stability.

Originating from one side of the finger guard's longer lateral edge is the semi circumferential pivoting finger clasp 12. It is conjoined to the finger guard 4 by a substantially thin and narrow juncture or flexion pivot 10. The flexion pivot 10 is a pivot juncture that permits finger clasp 12 rotations by virtue of its flexibility. As the finger clasp 12 is rotated, the flexion pivot 10 will flex and bend to accommodate the degree of rotation (FIGS. 2A to 2C). Note relative to the finger guard, finger clasp 12 is substantially less wide. This reduction in width is intended to accommodate and correlate with the underside or flexor portion of a finger. The width ideally permits free finger flexion while simultaneously maximizing operational stability.

Molded into the finger clasp's 12 termination is a somewhat raised, rectangular extrusion, that contains a number of saw teeth-like increments (seen close-up in FIG. 4A). These collective increments of clasp ratchet 14 are designed to interlock with the finger guard's 4 clasp securing extension 18 when it is adequately rotated (FIGS. 2C, 4B, 4C). The ratchet 14 has a desirable number of ratchet teeth to permit user determined constriction around a finger. Surrounding the clasp ratchet 14 is a box-like containing structure or ratchet stabilizer 16. The stabilizer 16 serves to laterally stabilize the ratchet during its interlocking engagement with the finger guard's securing extension 18 (FIGS. 3A, 3B and 4B). This reduces the incidence of disengagement during operation.

Attached to the finger guard's 4 opposite longer lateral (opposite of the finger clasp) edge is the guard securing extension 18. It is a substantially elongated and narrow extrusion off of the finger guard 4. Formed toward its termination are two raised engaging teeth or clasp securing ratchet 20. The guard securing extension's opposing orientation with the finger clasp is designed to receive the finger clasp 12. As stated above, as the finger clasp 12 is desirably rotated along its flexion pivot 10, it will engage the securing extensions 18 clasp securing ratchet with its finger clasp ratchet 14 to form an interlocking union (FIGS. 2C, 4B and 4C)

The instrument cleaners 2 secondary portion or cleaning foam 22 portion is a rectangular volume of foam open cell foam. It has an aspect ratio that correlates with the swiping platforms 6 rectangular dimension. The foam's 22 absorbency is optimized to receive to hold applied medicaments of all viscosities. Furthermore, the cleaning foam's 22 composition desirably maintains operational integrity during interaction with any number of medicaments. Additionally, the foam 22 can be colored to mask the appearance of unsightly bio debris. Note, the cleaning 22 foam has two functional surfaces one surface has an adhesive layer 24 that serves as the attachment mechanism to the swiping platform 6 (FIG. 1C). The adhesive layer 24 is a non-toxic composition that is desirably impervious to de-lamination when exposed to wetting agents or other medicaments. The second surface is the portion or area where medicaments are applied and bio debris are deposited during operation. Lastly, the cleaning foam 22 is desirably thick to optimally hold applied medicaments and furthermore to provide optimal thickness to envelop debris from an instrument.

The instrument cleaner with finger guard 2 may be made from any number of suitably rigid materials. It is ideally a singularly injection molded disposable plastic material. However, it can be made from any number of non disposable materials such as metal, or any other suitable composite. Furthermore it can be made as separate pieces that are assembled for operation. The cleaning foam 22 may be made from any foam that is suitably dense and absorbent to optimally accept medicaments and simultaneously maintain operational integrity while interacting with wetting agents or medicaments. The foam may be a separately attached the finger guard 4 via an adhesive or may be joined via an over molding process. Regarding adhesives, any number may be used providing tissue compatibility is not compromised by their employment.

Alternative Embodiments

There are various configuration possibilities with regard to the instruments cleaner with finger guard.

FIGS. 9A to 9B show an alternative finger mounted cleaning instrument 2 with an angled swiping platform 36 designed to ergonomically position the cleaning foam 22 toward the operator's field of operation. FIGS. 10A to 10B show various views of an instrument cleaner 2 with a similarly angled swiping platform 36. Added to the finger guard 4 is the addition of a barrier or instrument deflection guard 38. The instrument deflection guard 38 is designed to contain errant sharpening motions.

Figure 11:
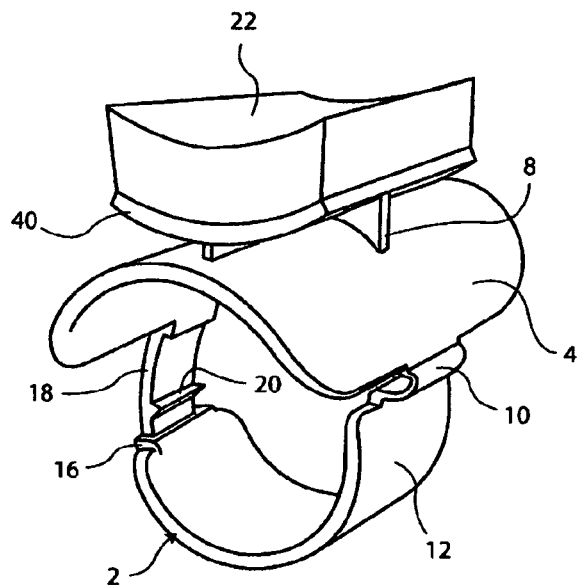
FIG. 11 shows an alternative embodiment having a concave swiping platform.
Figure 12:
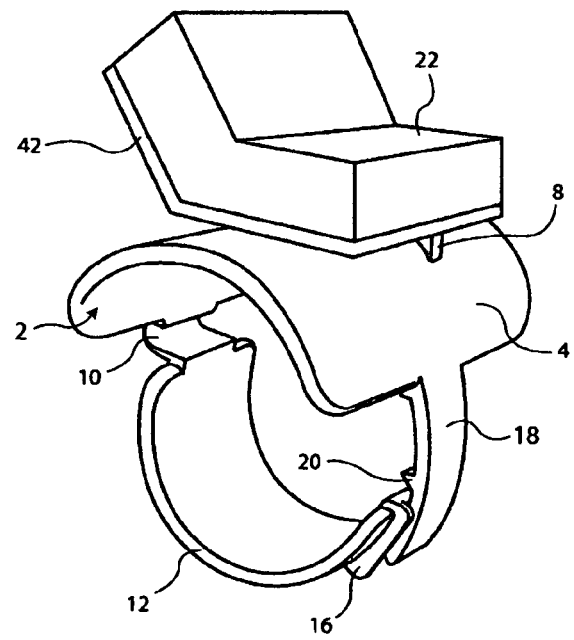
FIG. 12 shows an alternative embodiment having a variably angled swiping platform.
Figure 13A:
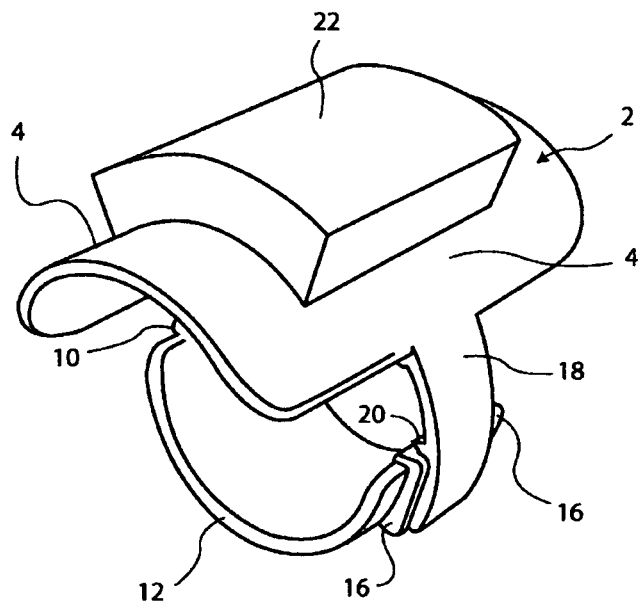
FIGS. 13A to 13B show an instrument cleaner with no swiping platform. The cleaning foam is instead adhered to the finger guard's convex surface.
Figure 13B:
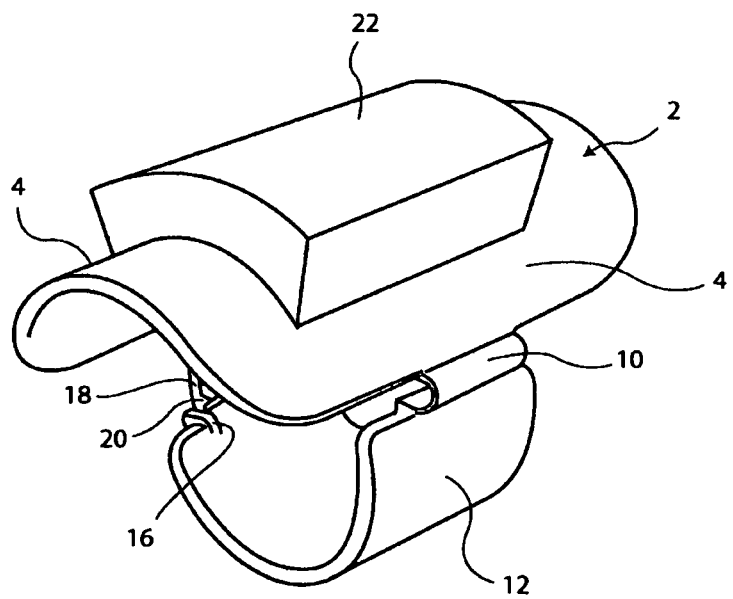
Figure 14A:
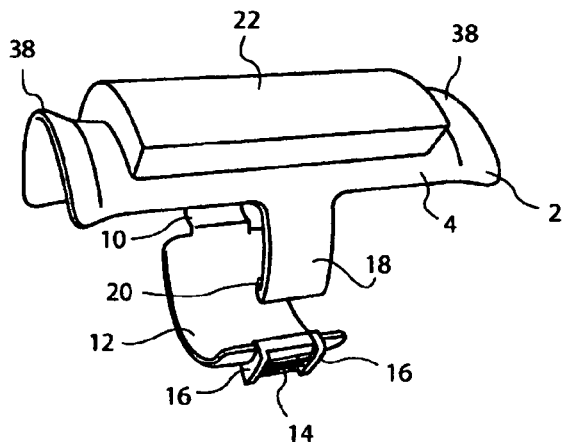
FIGS. 14A to 14C show an alternative embodiment having a curved swiping surface and instrument deflection guards formed into the expanse's ends.
Figure 14B:
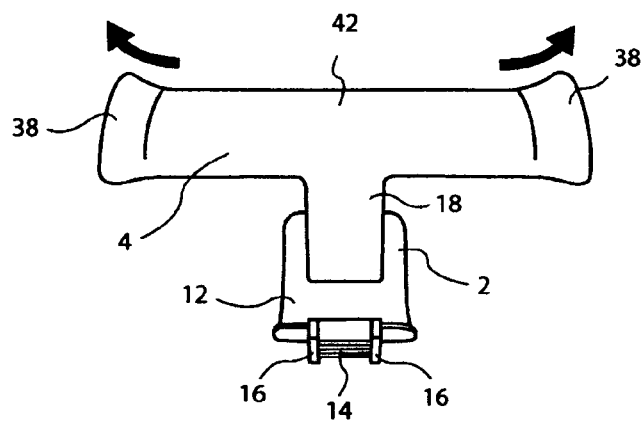
Figure 14C:
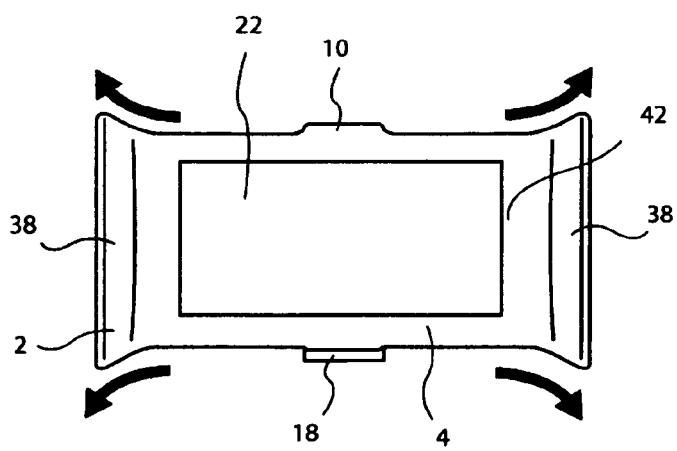

FIG. 11 shows an alternative instrument cleaner 2 embodiment having a concave swiping platform 40. The concave curvature is design to gently contain swiping motions to reduce potentially errant instrument cleaning motions. FIG. 12 shows an alternative instrument cleaner 2 having a variably angled swiping platform 42. The varied angulations increase available cleaning surface area, ergonomics and safety FIGS. 13A to 13B show an instrument 2 cleaner without a swiping platform. In this embodiment, the cleaning foam 22 is directly adhered to the finger guards 4 convex surface. FIGS. 14A to 14C show another instrument cleaner 2 with flared deflection guards 38 incorporated onto the finger guard's 4 terminations. These gently tapered flares are designed to deflect errant sharpening motions away from a user.

Figure 15A:
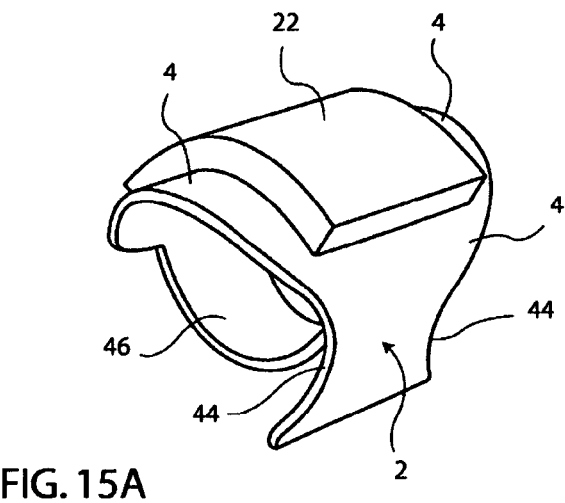
FIGS. 15A to 15C show an instrument cleaner with finger gripping contours in place of a pivoting finger clasp and ratchet system.
Figure 15B:
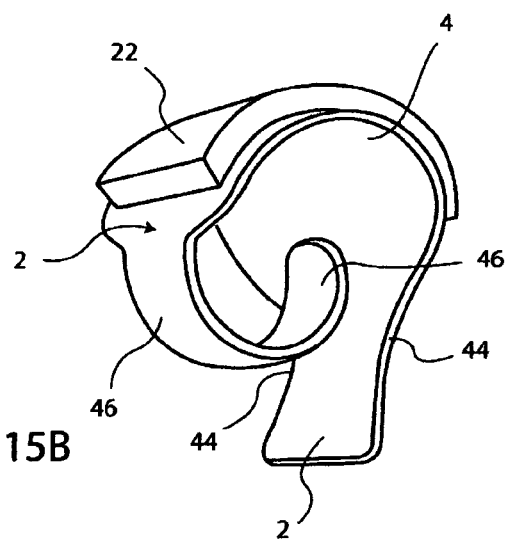
Figure 15C:
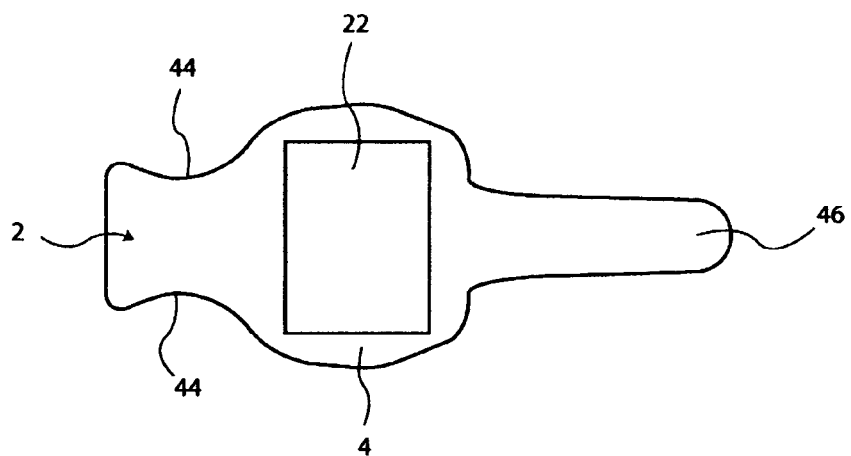
Figure 16A:
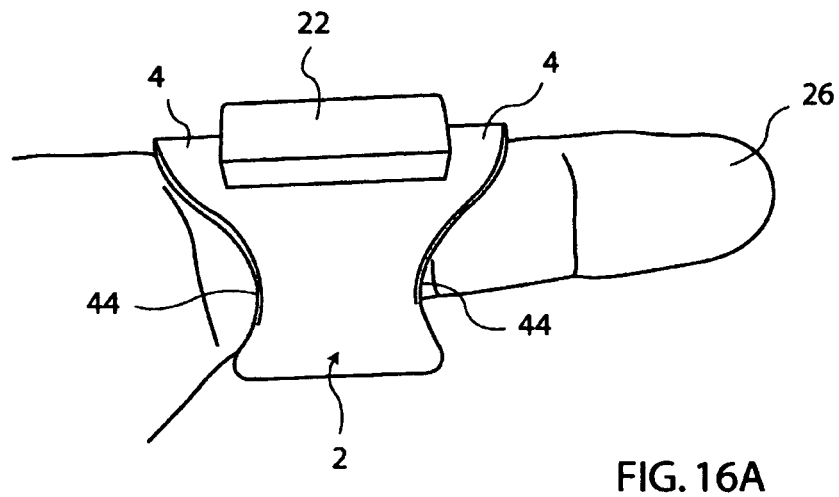
FIGS. 16A and 16B show an operator securing the instrument cleaner by flexing a finger to engaging the finger gripping contours.
Figure 16B:
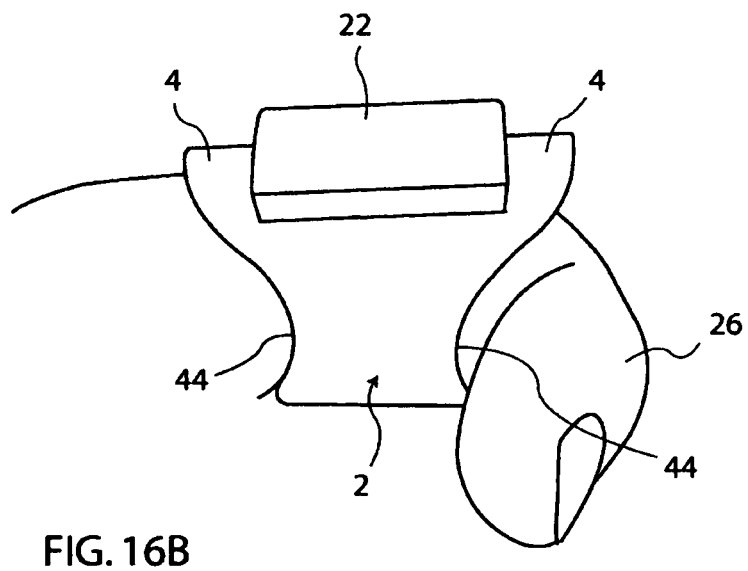

FIGS. 15A to 15C show an instrument cleaner 2 embodiment without a swiping platform 6 and without an interlocking finger clasp 12 and clasp ratchet 14 system. This embodiment utilizes a semi-circumferential frictional gripping coil 4 to wrap around the underside or flexor portion of a finger. The gripping coil 46 has a non-connective termination that is adaptive to various finger sizes. Additionally, it has engaging grooves or finger gripping contours 44 formed into the finger guards 4 periphery. These are designed to engage an operators 28 flexed finger (FIGS. 16A to 16B).

Figure 17A:
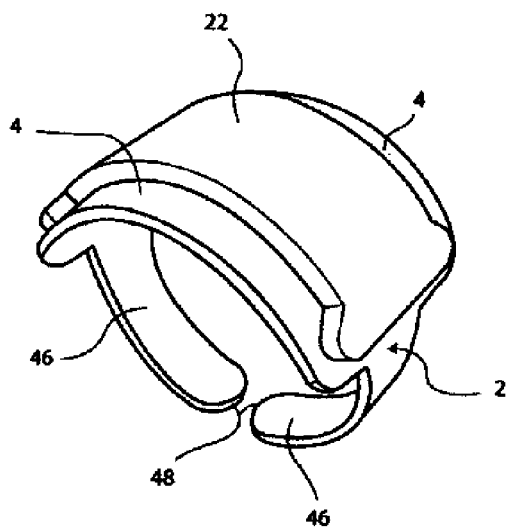
FIGS. 17A and 17B show an instrument cleaner with two gripping finger coils separated by a flexion gap.
Figure 17B:
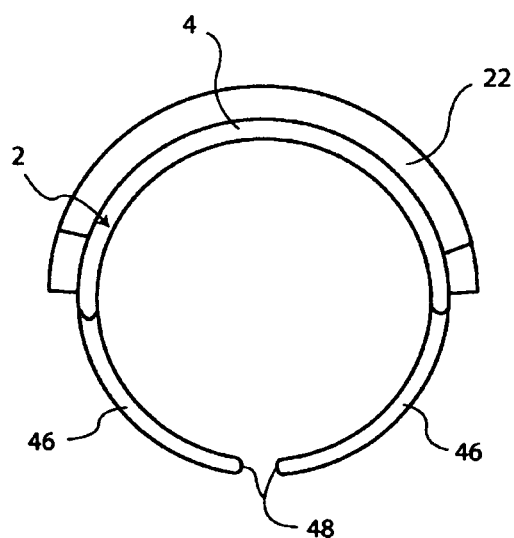
Figure 18:
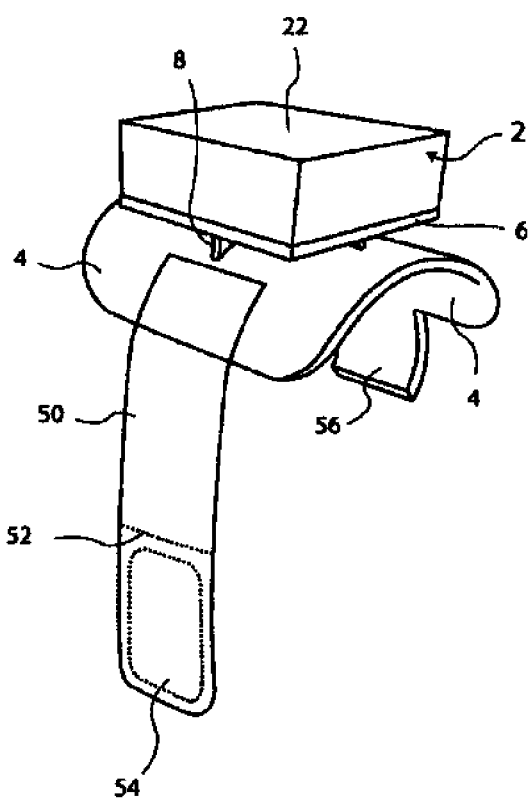
FIGS. 18A to 18C show various views of an instrument cleaner with an adhesive securing strap.
Figure 18:
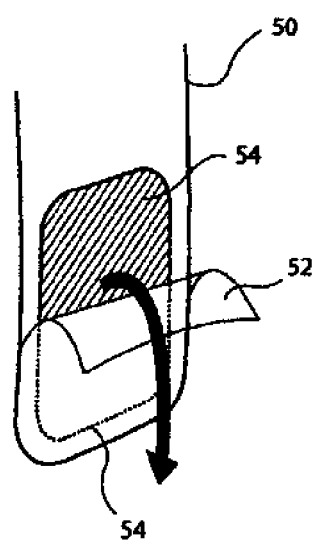

FIGS. 17A to 17B show an instrument 2 cleaner with two finger gripping coils 44. Their non-terminated ends result in a flexion gap 48. The flexion gap 48 is designed to expansively separate to frictionally engage and accommodate a variety of finger diameters. FIGS. 18A to 18C show various views of an instrument cleaner 2 that utilizes an adhesive securing strap 50 to provide operational stability (FIG. 18A). The strap 50 is a plastic ribbon material that has a removable cover 52. Removing the cover 52 exposes a securing adhesive 54 when removed (FIG. 18B). This exposed adhesive can then be adhesively attached to an adhesive securing expanse to form a cylindrical union (FIG. 18C).

Figure 19A:
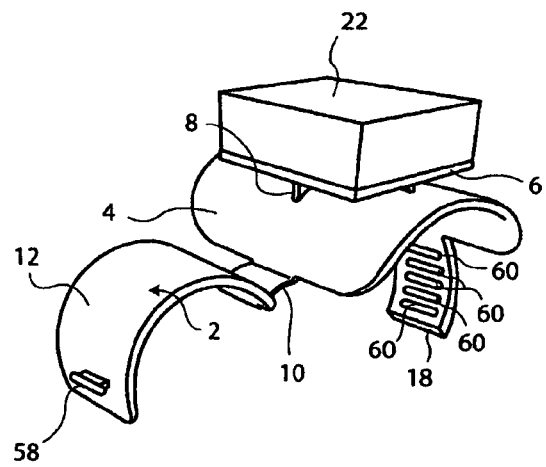
FIGS. 19A and 19B show an instrument cleaner with a snapping extrusion formed onto the clasp and a number of snapping apertures formed into the clasp securing extension.
Figure 19B:
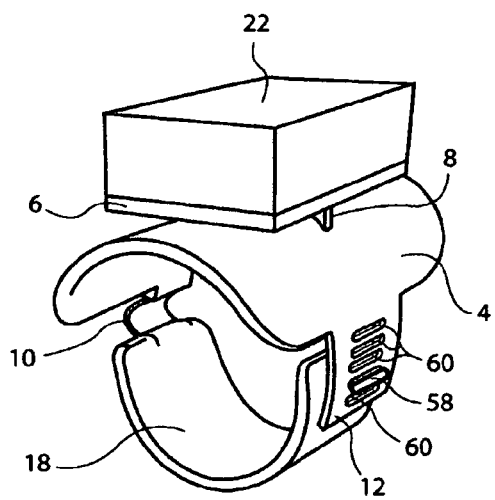
Figure 20:
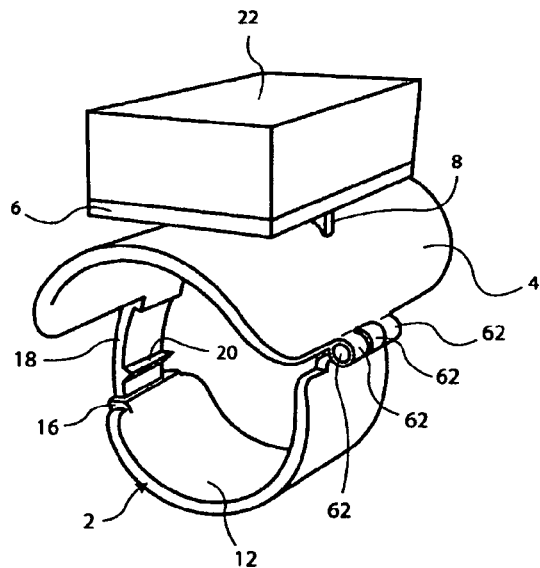
FIG. 20 shows views of cleaning foam having peripherally indented debris traps.
Figure 21:
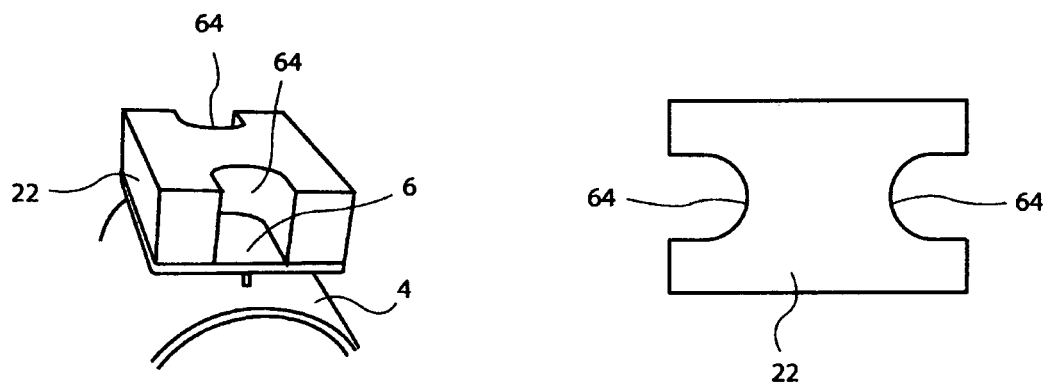
FIG. 21 shows views of cleaning foam having cylindrical debris traps formed within its interior.
Figure 22:
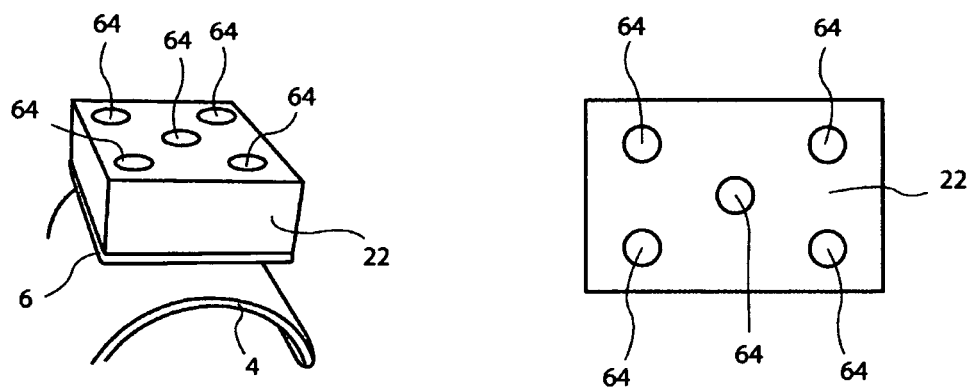
FIG. 22 shows a cleaning foam 22 with debris traps 64 formed into its interior.

FIGS. 19A to 19B show an instrument cleaner 2 with a snapping extrusion 58 formed onto the finger clasp 12 and a number of snapping apertures 60 formed into the clasp securing extension 18. They are designed to have a snapping interlocking engagement rather than a ratchet and pawl type of engagement. FIG. 20 shows a non-disposable metal instrument cleaner 2 with a pivot hinge 62. FIG. 21 shows a cleaning foam 22 embodiment that has debris traps 64 formed into its periphery. FIG. 22 shows a cleaning foam 22 with debris traps 64 formed into its interior. The debris traps 64 are traversing cavities or openings that serve as sub-surface entrapment depositories of or reservoirs for medicaments.

Operation FIGS. 5a-8d

Figure 5A:
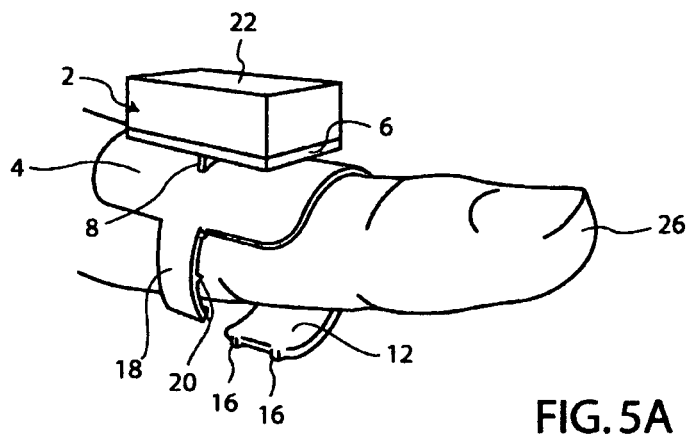
FIGS. 5A to 5C show an operator securing an instrument cleaner to a finger in a progressive sequence.
Figure 5B:
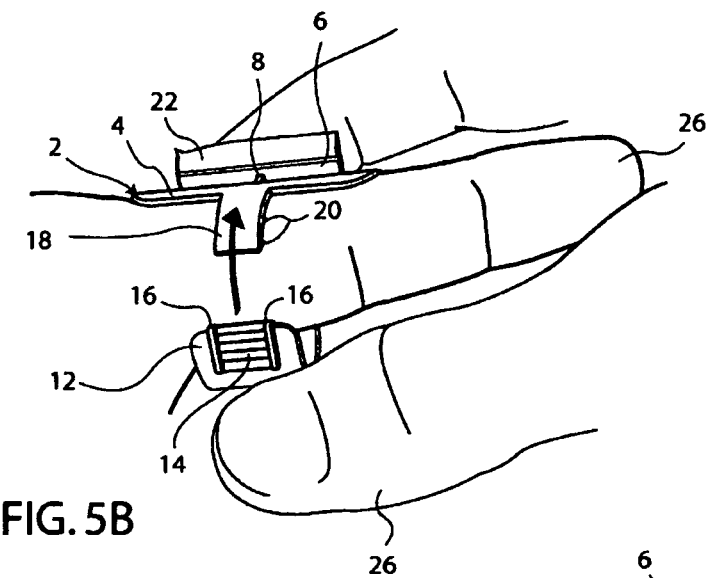
Figure 5C:
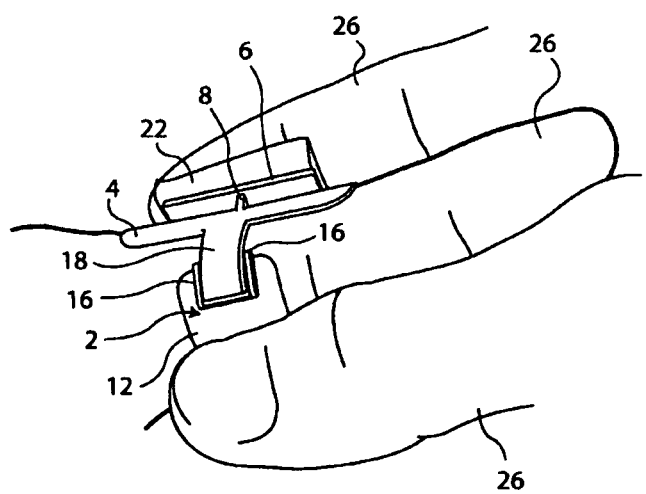

Using the finger mounted instrument cleaner first depends upon selecting a desired finger to place it on. Once selected, an operator 26 first positions and places the concave aspect of the finger guard 4 onto the extensor portion of the finger (FIG. 5A). Next, using the other hand, the operator 26 rotates the finger clasp 12 along the flexion pivot 10 (FIG. 5B) until the clasps engages flexor portion of the finger. To secure the instrument cleaner onto the finger, the finger clasp 12 and clasp ratchet 14 teeth are desirably engaged with the clasp securing extension's 18 clasp securing ratchet 20 (FIG. 5C). After engagement, the degree of constriction can be modulated by progressively tightening or loosening the clasp ratchet 14 until a comfortable level has been achieved.

Figure 6A:
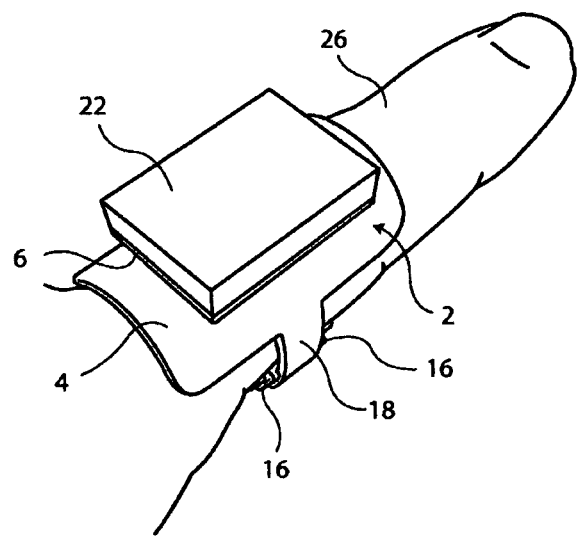
FIGS. 6A to 6B show views of an operator applying a medicament to the absorbent cleaning foam.
Figure 6B:
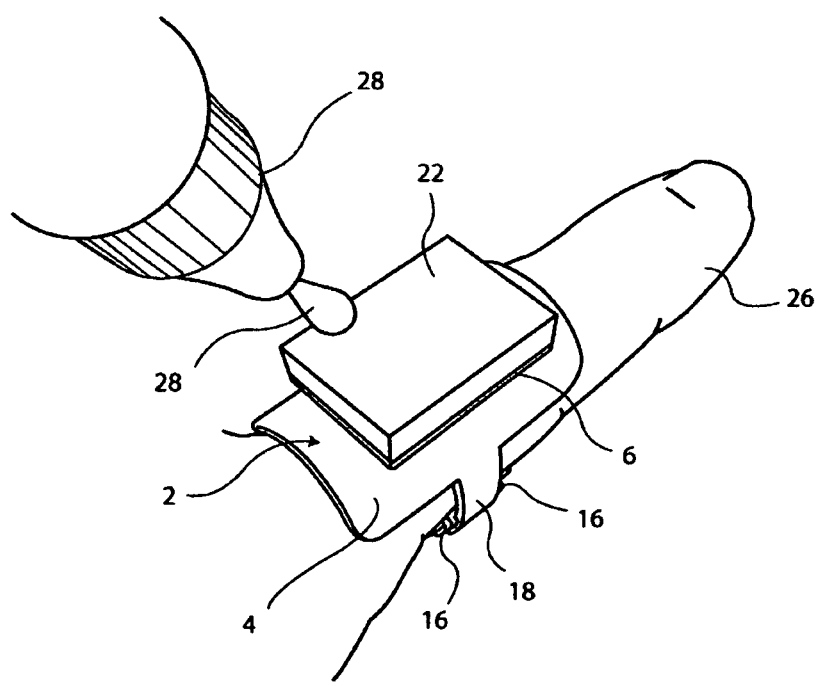

After the instrument cleaner 2 is securely on a finger (FIG. 6A), the operator 26 may next apply a desired medicament 28 to the absorbent cleaning foam 22 (FIG. 6B). The open cell nature of the foam 22 will readily absorb and hold the medicament 30. Applying medicament 28 has important operational functions. Firstly it facilitates debris 34 removal from an operative instrument 30 while simultaneously sterilizing the instrument 30. Secondly, it serves as a medicament delivery vehicle every time the instrument 30 is debrided and reinserted into an operative field (the instrument will introduce medicament into tissue).

Figure 7A:
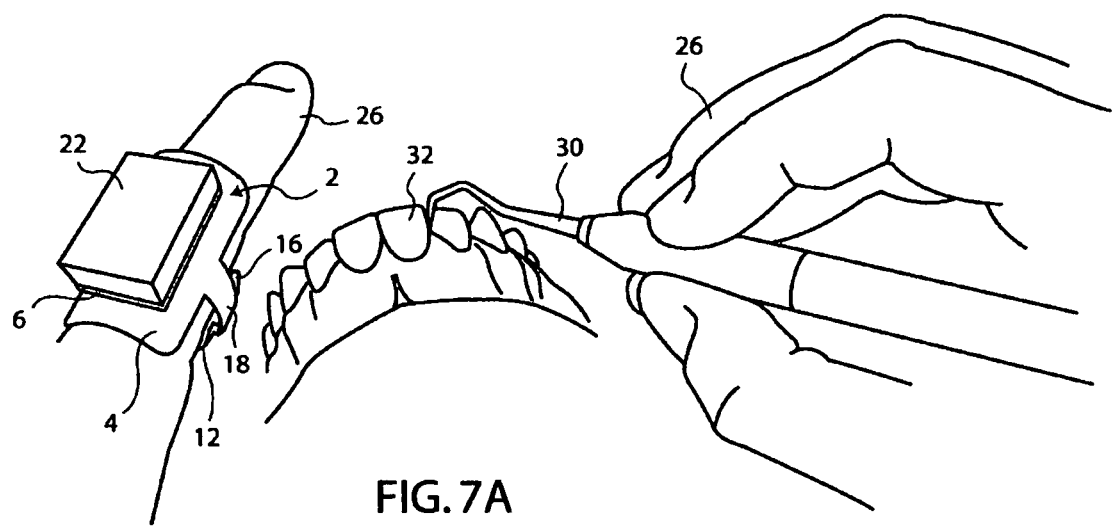
FIGS. 7A to 7B show views the finger mounted instrument cleaner in an operative environment.
Figure 7B:
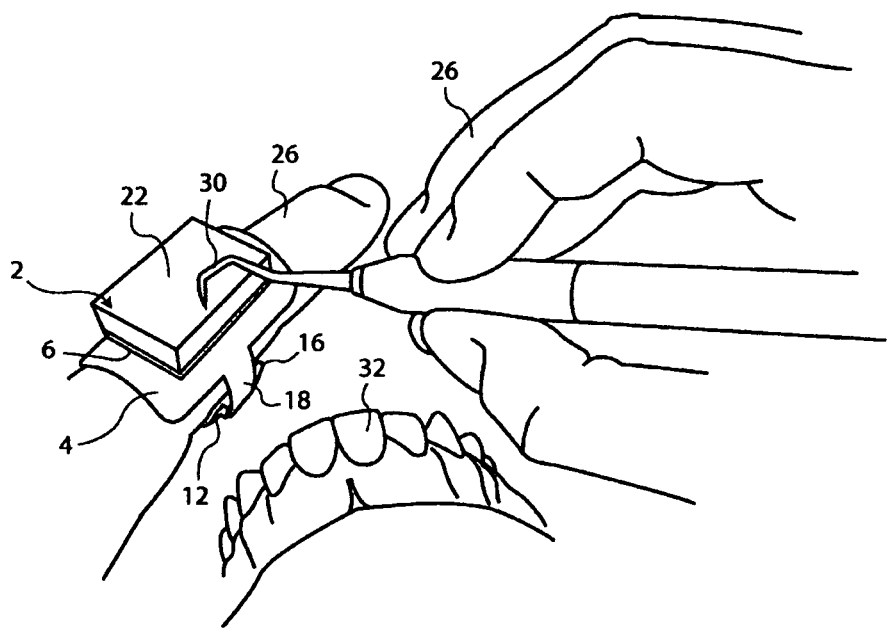
Figure 8A:
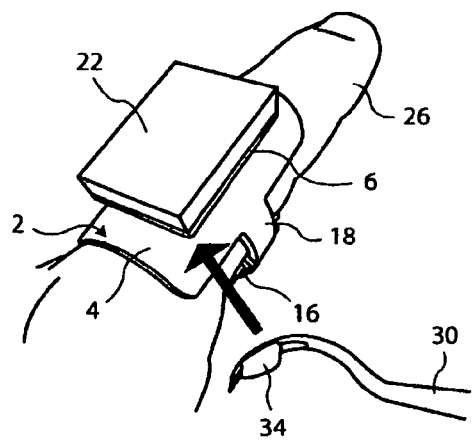
FIGS. 8A to 8D show accumulated debris being removed from an operative instrument in a progressive sequence.
Figure 8B:
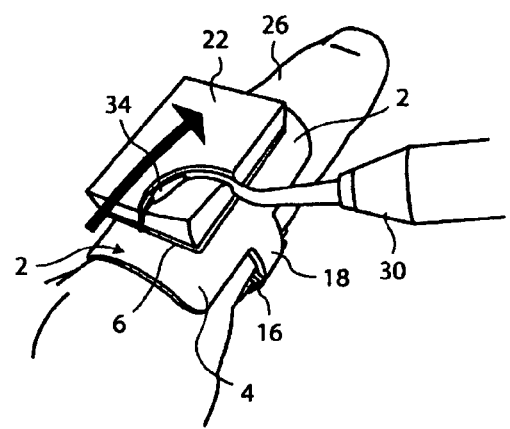
Figure 8C:
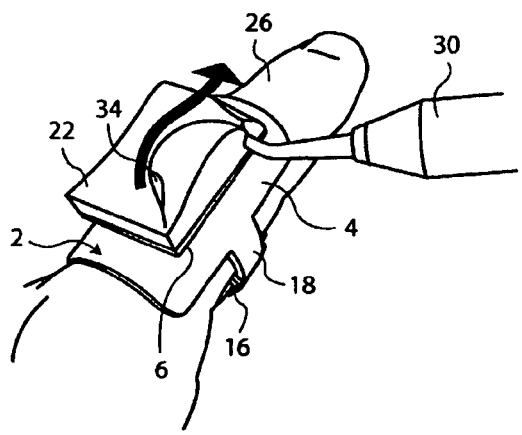
Figure 8D:
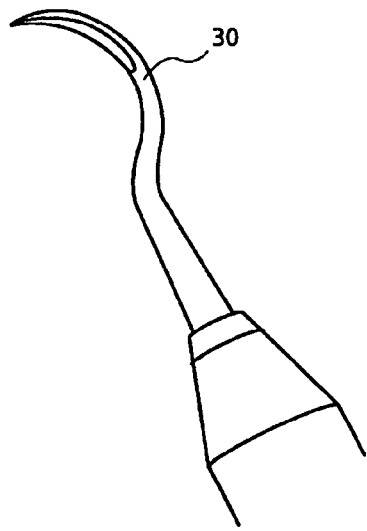

Next, for procedural efficiency, the operator 28 desirably positions the instrument cleaner 2 to provide optimal ergonomic access (FIG. 7A). As a patient's dentition 32 is scaled and cleaned, the operator 26 removes accumulated debris 34 as needed (FIG. 7B). To effectively remove accumulated debris 34, an operator 26 first guides the instrument 30 to the cleaning foam's 22 surface (FIG. 8A). Next, the operator 26 pokes and compressively slides the instrument 30 in a desired manner across the cleaning foams 22 surface (FIG. 8B). During the instruments 32 contact and engaging envelopment with the cleaning foam 22, the debris 34 becomes entrapped in the medicated surface (FIG. 8C). The result is a cleaned and sterilized instrument 30 (FIG. 8D). As the operative procedure continues, this cleaning process may be repeated as needed. Additional medicament can be re applied to the cleaning foam 22 at any point of a procedure (not shown).

CONCLUSIONS, RAMIFICATIONS, AND SCOPE

Accordingly, the reader will see that the disposable finger mounted instrument cleaner can be used to clean instrumentation of debris with ergonomic efficiency and maximum safety to the user. This is accomplished with minimal disruption to procedural focus resulting in a procedural efficiency that promotes greater concentration on patient care and safety. In addition, the single patient use permits easy disposal thus negating the need for time consuming and undesirable autoclaving. Moreover, the ability to pre-medicate the operative surfaces brings enhanced patient care that is significantly more difficult with other conventional means.

Furthermore, the finger mounted instrument cleaner has additional advantages in that It permits a variety of configurations for potentially demanding applications, It can be pre-medicated with specialized antiseptics for fingertip access Color-coded varieties can help distinguish specialized varieties or mask undesirable bio-debris.

Configurations can be made such that debris can be trapped sub-surface, greatly reducing the potential for exposing contaminants to undesirable surfaces.

Although the description above contained much specificity, these should not be construed as limiting the scope of the invention but merely as providing illustrations of some of the presently preferred embodiments of this invention. The disposable finger mounted instrument cleaner can assume any shape, size, or dimension that best allows for optimal cleaning of instruments. For example, the finger guard may assume any shape size or volumetric dimension as needed for optimal instrument cleaning and operator protection. It may also be comprised of any material that promotes optimal security, stability and comfort. This includes all manners of synthetics, metals or other organic materials. Also, any number of specialized coatings may be applied to all exterior or interior aspects of the cleaner. This includes adhesives, infection control substances, or any other operative enhancing substances.

The cleaning foam may have any size, shape and thickness as needed for optimal instrument cleaning. Any durometer of foam may be used. The foam may be layered with various foams or other materials. The foam may have any number of openings or insets to serve as debris traps for bio debris. The foam may also be open or closed cell to ensure optimal collection absorption, compressibility, abrasiveness, stability, protection, and comfort. Additionally, the cleaning foam may have additional design considerations for sharps or bladed instruments. These may include channels or pockets with slice resistant coatings or laminated layers of appropriately protective materials.

The instrument cleaner may also be optimized for the delivery of any desirable substance to a surface. Such examples are medicaments or other agents for the purposes of infection control and/or introduction of therapeutic substances. The instrument cleaning foam may also be pre-medicated with any of these appropriate substances.

Additionally, any number of attaching or securing means may be incorporated to ensure operational stability. For example, any number of ratchets, straps, snapping mechanisms or adhesive may be applied to any aspect of the device to aid attachment to the operator. Gripping mechanisms such as Velcro or magnets may also be employed. Lastly, any of the above alternatives may be incorporated to any degree. Any features may be included or completely eliminated for optimal cleaning function.

Thus, the scope of the invention should be determined by the appended claims and their legal equivalents, rather than by the examples given.

We claim:

1. A finger mounted instrument cleaner to adjustably interlock around a finger comprising:
   (a) a protective ring consisting of a semi-cylindrical finger guard which correlates with the extensor and lateral portions of a finger from the knuckle to a distance beyond the first phalange, and
   (b) a semi-cylindrical finger clasp conjoined to said finger guard's lateral edge by a flexion pivot therein possessing and terminating in a raised extrusion containing clasp ratchets, wherein said ratchets are surrounded by a ratchet stabilizer-interlocking ratchet system at its termination, and
   (c) a clasp securing extension attached to said finger guard's opposite side, possessing an interlocking two-tooth clasp securing-ratchet system at its termination to facilitate a variably circumferential interlocking union when engaging said finger clasp, and
   (d) an elevated rectangular planar swiping platform attached to said finger guard by a series of platform supports wherein said platform is dimensionally smaller than said finger guard, and
   (e) a volume of foam to adhesively attach to said swiping platform, wherein said foam correlates with said swiping platform's rectangular dimension.

2. A finger mounted instrument cleaner to adjustably interlock around a finger comprising:
   (a) a protective ring whose first portion consists of a semi-cylindrical finger guard having tapered, flared deflection guards at its terminations which correlate with the extensor and lateral portions of a finger from the knuckle to a distance beyond the first phalange, and
   (b) a semi-cylindrical finger clasp conjoined to said finger guard's lateral edge by a flexion pivot therein possessing and terminating in a raised extrusion containing clasp ratchets, wherein said ratchets are surrounded by a ratchet stabilizer-interlocking ratchet system at its termination, and
   (c) a clasp securing extension attached to said finger guard's opposite side, possessing an interlocking two-tooth clasp securing-ratchet system at its termination to facilitate a variably circumferential interlocking union when engaging said finger clasp, and
   (d) a volume of foam to adhesively attach to said finger guard, wherein said foam is dimensionally smaller than said finger guard.

* * * * *